United States Patent
Roby et al.

(10) Patent No.: US 6,287,499 B1
(45) Date of Patent: Sep. 11, 2001

(54) PROCESS OF MAKING BIOABSORBABLE BLOCK COPOLYMER FILAMENTS

(75) Inventors: Mark S. Roby, Kilingworth, CT (US); Jerry Ying Jonn, Raleigh, NC (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

(21) Appl. No.: 09/391,845

(22) Filed: Sep. 8, 1999

Related U.S. Application Data

(60) Provisional application No. 60/103,761, filed on Oct. 9, 1998.

(51) Int. Cl.$^7$ .............................. D01D 5/12; D01D 10/02
(52) U.S. Cl. ................................... 264/210.5; 264/210.8; 264/211.14; 264/211.17; 264/211.24; 264/235; 264/235.6; 264/342 RE
(58) Field of Search ........................... 264/210.5, 210.8, 264/211.14, 211.17, 211.24, 235, 235.6, 342 RE

(56) References Cited

U.S. PATENT DOCUMENTS

| | | |
|---|---|---|
| 3,092,891 | 6/1963 | Baratti . |
| 3,106,442 | 10/1963 | Compostella et al. . |
| 3,630,205 | 12/1971 | Listner . |
| 4,122,129 | 10/1978 | Casey et al. . |
| 4,438,253 | 3/1984 | Casey et al. . |
| 4,826,945 | 5/1989 | Cohn et al. . |
| 4,911,165 | 3/1990 | Lennard et al. . |
| 5,019,093 | 5/1991 | Kaplan et al. . |
| 5,059,213 | 10/1991 | Chesterfield et al. . |
| 5,217,485 | 6/1993 | Liu et al. . |
| 5,252,701 | 10/1993 | Jarrett et al. . |
| 5,342,557 | 8/1994 | Kennedy . |
| 5,456,696 | 10/1995 | Liu . |

FOREIGN PATENT DOCUMENTS

| | | |
|---|---|---|
| 415783 | 3/1991 | (EP) . |
| 707044 | 4/1996 | (EP) . |
| 786259 | 7/1997 | (EP) . |
| 848089 | 6/1998 | (EP) . |
| 2008135 | 5/1979 | (GB) . |
| 1588081 | 4/1981 | (GB) . |
| 6-93252 | 4/1994 | (JP) . |

*Primary Examiner*—Leo B. Tentoni

(57) ABSTRACT

A method for making bioabsorbable block copolymer includes extruding a mixture of first polymeric component particles with second polymeric component particles under conditions sufficient to cause transesterification. The resulting block copolymer filaments can be used to form surgical sutures.

11 Claims, 1 Drawing Sheet

PROCESS OF MAKING BIOABSORBABLE BLOCK COPOLYMER FILAMENTS

This Application claims priority of Provisional Application Ser. No. 60/103,761 filed Oct. 9, 1998

BACKGROUND

1. Technical Field

The present disclosure relates to methods for making block copolymers for use in producing surgical articles such as sutures, and more particularly to a method for making bioabsorable block copolymers by transeterifying two or more pre-polymers.

2. Background of Related Art

Methods for making monofilaments that are suitable surgical sutures generally include the steps of extruding a least one bioabsorable or nonbioabsorable polymer to provide filaments, drawing, or stretching the solidified filaments to achieve molecular orientation and annealing th edrawn filaments to relieve internal stresses. Se, e.g. U.S. Pat. Nos. 392,891, 3,106,442, 3,630,205, 4,911,165, 5,217,485 and U.K. Patent Specification No. 1,588,081 and European Patent Application No. 415,783.

Examples of copolymers used to fabricate surgical articles such as sutures include, for example, diblock copolymers, symbolized by an AB block structures, or triblock copolymers, sybolized by an ABA block structure, wherein A and B present polymeric chain having repeating units of a given type wherein the A chain and the B chain are each normally derived from different monomer components of different combinations of monomers. See, e.g., U.S. Pat. No. 4,826,945 to Cohn et al. and U.S. Pat. No. 4,438,253 to Casey et al.

Transesterification that occurs in bioabsorbable polyesters produces a high degree of shuffling and randomness which prevents the resulting transesterfied copolymer from having a well defined block structure. See, e.g., U.S. Pat. No. 5,252,701 to Jarrett et al. Such randomness also affects the properties of the final surgical product, such as in vivo strength retention as well as other chemical and physical properties such as solubility, brittleness, and rate of absorption. It would be desirable to have a simple method to make a surgical article from a bioabsorbable block copolymer through a transesterification reaction while maintaining a well defined block structure.

SUMMARY

Methods for making a bioabsorbable block copolymer are provided herein. The methods include melt extrusion of two polymeric components at time and temperature conditions such as to effect transesterification and formation of a copolymer having well defined block structure with little shuffling between the blocks. The polymeric components can each be a homopolymer or a copolymer.

BRIEF DESCRIPTIONS OF THE DRAWINGS

Figure 1:
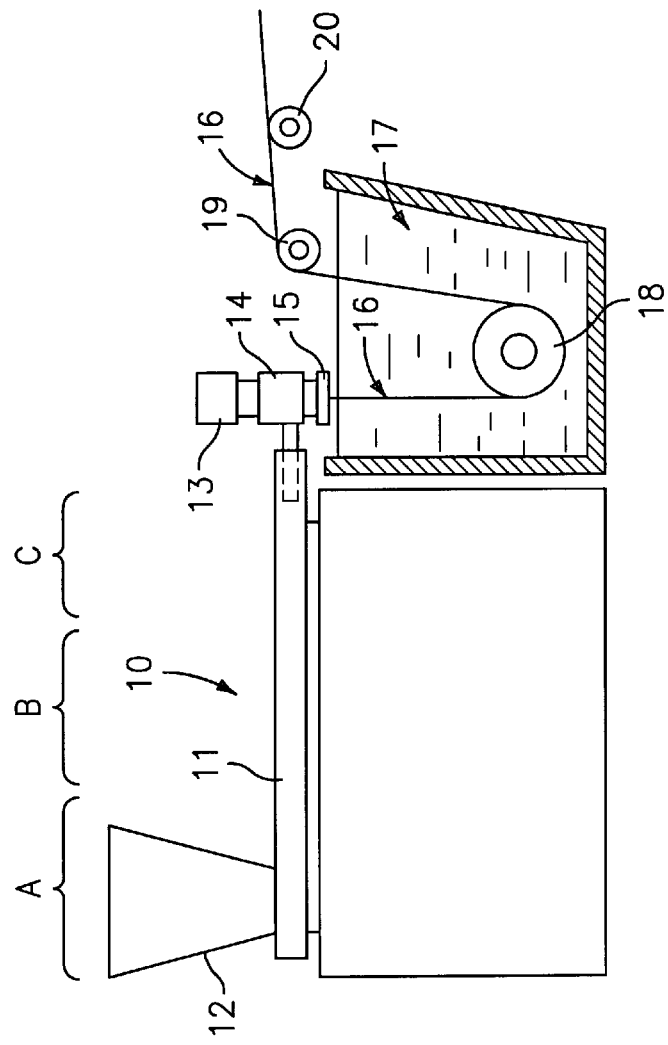
Figure 2:
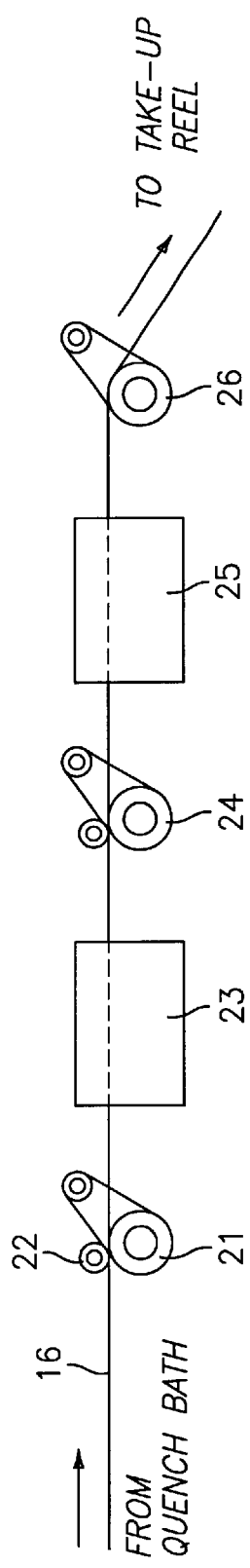

Various embodiments are described herein with reference to the drawings, wherein FIG. 1 is a schematic illustration of an apparatus which is suitable for carrying out the method described herein to form a filament;

FIG. 2 is a schematic illustration of further processing, including stretching and heating, of the resulting filament.

DETAILED DESCRIPTION OF PREFERRED EMBODIMENTS

Block copolymers are made using the methods described herein by mixing pellets or powder of a first polymeric component with pellets or powder of a second polymeric component, loading the mixed pellets or power into an extruder, extruding the mixture of polymers and optionally quenching the extruded copolymer. The temperature and duration of heating within the extruder are controlled so as to effect transesterification of the two polymeric components while maintaining a well defined block structure of the resulting copolymer.

The extrusion temperature must be at least a minimum to accomplish transesterification, yet it should not be so high as to degrade the polyester starting materials or to generate substantial shuffling of the molecular structure of the starting polyesters. The term "shuffling" as used herein refers to mixing of the A block with the B block of the copolymer so that conventional block structure is lost and a random or segmented $(AB)_n$ structure is produced. While some small degree of shuffling may, as a practical matter, be unavoidable, substantial shuffling will convert conventional block structures (e.g., diblock AB or triblock ABA, or ABAB or ABABA, molecular structures etc.) to segmented block $(AB)_n$ or other random-type structures and should be avoided. Generally, the operating temperature ranges from about 50° C. to about 240° C., preferably from about 180° C. to about 220° C.

The residence time of the two polymeric starting components within the extruder should be sufficient to accomplish transesterification but insufficient to generate a substantial amount of shuffling or loss of block structure in the resulting copolymer. Suitable residence times will vary depending upon a number of factors such as the precise nature of the starting polyesters and the extrusion temperature and physical shape and size of the polymeric particles. The conditions employed should ensure a complete melt of the polymer mixture and a good mixing of the polymer starting materials. Generally, the higher the extrusion temperature, the shorter the residence time needed to obtain a desired degree of transesterification and vice versa. The residence time will normally be in the range of about 2 to about 20 minutes, preferably about 4 to about 10 minutes. The quench bath, which is provided to quickly cool the exiting filament, can be a bath of water maintained at a temperature of from about 25° C. to about 28° C.

The first and second polymeric components must be capable of undergoing transesterification to produce a block copolymer and can include any monomer or combinations of monomers known to form bioabsorbable polymers. The first and second polymeric components can be bioabsorbable homopolymers such as, for example, polyglycolide, polylactide, polydioxanone, polycaprolactone, polyalkylene oxide or polytrimethylene carbonate. Moreover, one or both of the first and second polyester components can be a copolymer made from a combination of monomers known to form bioabsorbable polymers. The aforementioned polymer starting materials are known to those with skill in the art and are in some cases commercially available in pellet or powder form. It should, of course, be understood that more than two polymeric starting materials can be employed to produce block copolymers having an ABC, ABCD, etc. structures. Addition of a catalyst is not generally necessary where the polymer used for mixing contains residual catalyst. However, small amounts of catalyst can be used if desired, to accelerate the transesterification in order to reduce the residence time.

Generally, the specific operating temperatures used to perform transesterification will depend on the particular mixture of polymer components and the ratios being used. The temperatures will typically be between the minimum melting temperature of the higher melting polymer and the maximum melting temperature of the lower melting polymer. For example, in the case of polymer components polydioxanone and polyglycolide, the temperatures will range from about 100° C., i.e., the minimum melting temperature for polydioxanone, to about 230° C., i.e, the maximum melting temperature of polyglycolide. In the event a greater amount of one polymer component is used, the operating temperature will approach the maximum operating temperature of that polymer component. Thus, e.g., in the case of polyglycolide being the major amount of the two polymer components used, the operating temperature will be closer to 230° C.

By keeping the processing temperature within the operating range given above shuffling can be kept below about 10%. That is, 90% or more of the resulting block copolymer will maintain the well defined block structure dictated by the polymeric starting materials with 10% or less having a segmented $(AB)_n$ or other type structure. The block structure of the resulting polymer can be measured by methods known to those skilled in the art such as, for example, $^{13}C$ NMR.

Extrusion apparatus suitable for use in the method described herein are known and described, for example, in U.S. Pat. Nos. 5,217,485 and 5,456,696, both of which are herein incorporated by reference.

FIG. 1 schematically illustrates a particularly useful apparatus for extrusion and quenching of a filament. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of polymer are introduced to the extruder through drier-hopper 12. Suitable polymers are discussed hereinbelow.

Motor-driven metering pump 13 delivers melt extruded polymer at a constant rate to spin pack 14 and thereafter through a spinneret 15 possessing one or more orifices of desired diameter to provide a molten filament 16 which then enters quench bath 17 where the filament solidifies. The quench bath is preferred, but optional, and preferably contains water. Shapes other than filaments can also be formed by an appropriately chosen die.

The distance filament 16 travels after emerging from spinneret 15 to the point where it enters quench bath 17, i.e. the air gap, can vary and can advantageously be from about 0.5 to about 100 cm. If desired, a chimney (not shown), or shield, can be provided to reduce the length of the air gap, e.g. from 1 to 10 cm, thereby isolating filament 16 from contact with air currents which might otherwise affect the cooling of the filament 16 in an unpredictable manner. Filament 16 is passed through quench bath 17 around driven roller 18 and over idle rollers 19 and 20. Optionally, a wiper (not shown) may remove excess water from the filament 16 as it is removed from quench bath 17. On exiting the quench bath the filament can be sent on for further processing such as aging and/or stretching operations.

For example, referring to FIG. 2, after the filament 16 exiting the quench bath 17 is passed over idler rollers 19 and 20, it is thereafter wrapped around a first godet 21. A nip roll 22 is provided to prevent slippage which might otherwise result from the subsequent stretching operation. Filament 16 passing from godet 21 is stretched in order to effect its orientation and thereby increase its tensile strength. Thus, in one type of stretching operation, generally suitable for smaller sutures, e.g., sizes 4/0 to 8/0, filament 16 is drawn through heating unit 23, which can be an oven chamber or a hot liquid (such as water and glycerol) trough, by means of second godet 24 which rotates at a higher speed than first godet 21, thereby stretching the filament from three to nine times its original length. Where heating unit 23 is an oven chamber, its temperature is advantageously maintained at from about 40° C. to about 140° C. and preferably from about 50° C. to about 120° C. In the case of larger sutures, e.g., sizes 2 to 3/0, it is preferred that heating unit 23 be a hot liquid trough or bath which is maintained at a temperature of from about 30° C. to about 98° C. and preferably from about 40° C. to about 90° C.

After the above mentioned operation it is preferred to pass the filament 16 through a second heating unit 25, e.g., maintained at a temperature of from about 40° C. to about 140° C. and preferably from about 50° C. to about 120° C., by means of a third godet 26 to heat-treat the filament 16 prior to the equilibration and annealing operations. This second heat treatment results in on-line relaxation, or shrinkage, of the filament, e.g., for a recovery of from about 85 to about 97 percent, and preferably from about 90 to about 95 percent, of the stretched length of the filament. In order to accommodate this on-line shrinkage in the filament, the third godet is driven at a speed which is somewhat less than that of the second godet.

Following stretching and orientation (and, optionally, the aforedescribed second heat treating step) filament 16 is taken up on a spool which is then set aside for a period of time sufficient to permit the filament to achieve a condition of equilibration. While the period of equilibration may vary depending on the particular copolymer composition employed and/or the conditions under which the copolymer is extruded, cooled and oriented, in most cases storage of the filament following its orientation for at about 2 hours, preferably at least about 24 hours and more preferably at least about 3 days. It is generally preferred that the spooled filament be stored at ambient temperature, e.g., 18° C.–23° C., and a dew point below –12° C.

Thereafter, annealing may be accomplished by shrinkage of the suture, e.g., for a recovery of from about 75 to about 95 percent, and preferably from about 80 to about 90 percent, of its stretched length.

In carrying out the annealing operation, the desired length of equilibrated suture may be wound around a creel and the creel placed in a heating cabinet circulated with nitrogen and maintained at the desired temperature, e.g., 70° C. After a suitable period of residency in the heating cabinet, e.g., about 20 minutes to 24 hours, the suture will have undergone shrinkage, e.g., to about 85% of the stretched length for sutures of sizes 2 to 3/0, to about 90% of the stretched length for sutures of sizes 4/0 and 5/0 and essentially no shrinkage in the case of sutures of sizes 6/0 to 8/0. The creel may be rotated within the heating cabinet in order to insure uniform heating of the filament or the cabinet may be of the circulating hot air type in which case uniform heating of the filament will be achieved without the need to rotate the creel. Thereafter, the creel with its annealed suture is removed from the heating cabinet and when returned to room temperature, the suture is removed from the creel, conveniently by cutting the wound filament at opposite ends of the creel.

The filament formed from the block copolymer described herein can be used as a monofilament or it can be combined with other filaments to form a suture. For example, the filament can be interwoven, knitted or braided with filaments of the same or different chemical composition to achieve optimum absorption characteristics. Spinning and braiding of fibers to form multifilament sutures can be accomplished by any known technique such as those described in U.S. Pat. Nos. 5,019,093 and 5,059,213, the disclosures of which are incorporated herein by reference.

The following examples will illustrate the features of this method.

EXAMPLE I

Monofilaments of a block copolymer of polyglycolide (first block) and poly(trimethylene carbonate/dioxanone) (second block) are prepared as follows:

A mixture of 60% by weight polyglycolide pellets and 40% by weight of pellets of a random copolymer of 65 mole % trimethylene carbonate/ 35 mole % dioxanone is prepared. Pellets of the aforementioned polymers may be prepared by conventional polymerization techniques known in the art. For example, a method for making particles of bioabsorbable polymer is disclosed in U.S. Pat. No. 5,342,557 to Kennedy, which is herein incorporated by reference. The pellet mixture is then loaded into the hopper of an extruder such as that described above, and processed under the following conditions to provide a size 3/0 monofilament suture.

|  | Process Conditions |
| --- | --- |
| Extruder screw, rpm | 3.1 |
| Barrel temperature, ° C., zone A | 195 |
| Barrel temperature, ° C., zone B | 200 |
| Barrel temperature, ° C., zone C | 208 |
| Barrel temperature, psi | 1400 |
| Barrel melt temperature, ° C. | 210 |
| Pump size, cc per revolution | 0.16 |
| Pump rpm | 12.6 |
| Pump temperature, ° C. | 209 |
| Pump pressure, psi | 1400 |
| Pump melt temperature, ° C. | 202 |
| Block temperature, ° C. | 209 |
| Clamp temperature, ° C. | 208 |
| Adapter temperature, ° C. | 208 |
| Filter type | Stainless |
| Filter screen, microns | 20 |
| Spinneret orifice diameter, mm | 1.25 |
| Number of spinneret orifices | 1 |
| Spinneret temperature, ° C. | 208 |
| Spinneret pressure, psi | 900 |
| Spinneret melt temperature, ° C. | 208 |
| Output, lb/hr per orifice | 0.5 |
| Air gap, cm | 5.0 |
| Quench bath temperature, ° C. | 17 |
| Driven roller, depth | 20 |
| Driven roller, rpm | 3 |

The resulting filaments are quenched, dried and stored on a spool.

EXAMPLE II

Monofilaments of a block copolymer of polyglycolide (first block) and poly(glycolide-co-lactide) are prepared as follows:

A mixture of 65% by weight polyglycolide pellets and 32% by weight of a random copolymer of 50 mole % glycolide/50 mole % lactide is prepared. Pellets of the aforementioned polymers may be prepared by conventional polymerization techniques known in the art. The pellet mixture is loaded into the hopper of an extruder such as that described hereinabove, and processed under the following conditions.

|  | Process Conditions |
| --- | --- |
| Extruder screw, rpm | 3 |
| Barrel temperature, ° C., zone A | 225 |
| Barrel temperature, ° C., zone B | 226 |
| Barrel temperature, ° C., zone C | 226 |
| Barrel pressure, psj | 750 |
| Barrel melt temperature, ° C. | 226 |
| Pump size, cc per revolution | 0.16 |
| Pump rpm | 37 |

-continued

|  | Process Conditions |
| --- | --- |
| Pump temperature, ° C. | 225 |
| Pump pressure, psi | 1000 |
| Pump melt temperature, ° C. | 226 |
| Block temperature, ° C. | 226 |
| Clamp temperature, ° C. | 227 |
| Adapter temperature, ° C. | 225 |
| Filter type | Stainless |
| Filter screen, microns | 20 |
| Spinneret orifice diameter, mm | 0.25 |
| Number of spinneret orifices | 40 |
| Spinneret temperature, ° C. | 228 |
| Spinneret pressure, psi | 1500 |
| Spinneret melt temperature, ° C. | 226 |
| Output, lb/hr per orifice | 1 |
| Quench temperature, ° C. | Air quench - ambient |

The resulting filaments are quenched, dried and stored on a spool.

While the above description contains many specifics and examples, these specifics and examples should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A method for making a bioabsorbable block copolymer filament comprising:

a) providing a mixture of particles of a first bioabsorbable polymeric component and particles of a second bioabsorbable polymeric component;

b) extruding said mixture of particles under conditions sufficient to transesterify the first and second polymeric components to produce a bioabsorbable block copolymer filament.

2. The method of claim 1 wherein the first and second polymeric components are both homopolymers.

3. The method of claim 1 wherein at least one of the first and second polymeric components is a copolymer.

4. The method of claim 1 wherein the first and second polymeric components are polymers made from one or more monomers are selected from the group consisting of glycolide, glycolic acid, lactide, lactic acid, caprolactone, dioxanone, polyalkylene oxide and trimethylene carbonate.

5. The method of claim 1 wherein the extruding step is conducted at a temperature in the range of about 50° C. to about 240° C.

6. The method of claim 1 further including the step of quenching the block copolymer filament.

7. The method of claim 1 further including the step of stretching the filament.

8. The method of claim 7 wherein said stretching is performed while heating the filament to a temperature of from about 40° C. to about 140° C.

9. The method of claim 7 further including the steps of relaxing the stretched filament.

10. The method of claim 9 wherein the relaxing is performed while heating the filament to a temperature of from about 40° C. to about 140° C.

11. The method of claim 1 further including the step of annealing the filament.

\* \* \* \* \*